United States Patent [19]
Hainfeld et al.

[11] Patent Number: 5,360,895
[45] Date of Patent: Nov. 1, 1994

[54] DERIVATIZED GOLD CLUSTERS AND ANTIBODY-GOLD CLUSTER CONJUGATES

[75] Inventors: James F. Hainfeld, Shoreham; Frederic R. Furuya, Williston Park, both of N.Y.

[73] Assignee: Associated Universities, Inc., Washington, D.C.

[21] Appl. No.: 988,338

[22] Filed: Dec. 9, 1992

Related U.S. Application Data

[63] Continuation-in-part of Ser. No. 661,215, Feb. 27, 1991, abandoned, which is a continuation-in-part of Ser. No. 317,388, Mar. 1, 1989, abandoned, which is a continuation-in-part of Ser. No. 212,545, Jun. 28, 1988, abandoned, which is a continuation-in-part of Ser. No. 41,054, Apr. 22, 1987, abandoned.

[51] Int. Cl.$^5$ .................... C07K 17/02; A61K 49/02
[52] U.S. Cl. ................ 530/391.5; 530/391.1; 530/391.3; 530/391.7; 530/391.9; 424/9; 424/1.29; 424/1.53; 436/547
[58] Field of Search ............... 530/391.1, 391.3, 391.5, 530/391.7, 391.9; 424/1.1, 9; 436/547

[56] References Cited

U.S. PATENT DOCUMENTS

| | | | |
|---|---|---|---|
| 4,454,070 | 6/1984 | Schmid | 534/10 |
| 4,460,559 | 7/1984 | Goldenberg | 424/1.1 |
| 4,671,958 | 6/1987 | Rodwell et al. | 424/85.91 |

OTHER PUBLICATIONS

Fackler, Jr. et al (1989) J. Am. Chem. Soc. 111:6434–5.
Hainfeld (1987) Science 236:450–453.
Castel et al (1985) J. Hist. Chem. Cytochem: 33(10):1015–1025.
Goodman et al (1983) Exp. Cell Res 144:209–214.
Lipka et al (1985) in G. W. Bailey ed., Proceedings of the 43rd Annual Meeting of the Electron Microscopy Soc. Am. San Francisco Press Inc, San Francisco pp. 718–719.
Manassero et al (1979) JCS, Chem. Commun No. 9 385–386.
Martin et al (1981) Biochemistry 20:4229–4238.
Moeremans et al (1984) J. Immunol. Methods 74:353–360.
Perry et al (1986) Cytogenet Cell Genet 41:121–125.
Reardon et al (1984) Biochemistry 23:3849–3856.
Safer et al (1986) J. Inorg. Biochem. 26:77–91.
Yang et al (1984a) Biochemistry 23:3857–3862.
Yang et al (1984b) Biochemistry 23:3863–3868.
van der Velden et al (1981) Recueil J. Ro. Neth. Chem. Soc. 100/4:148–152.
Hainfeld (1988) Nature vol. 333:281–282.
Lipka et al (1983) J. Ultrastructure Res 84:120–129.
Safer et al (1986) J. Inorg. Biochem. 26:77–91.
Wall et al (1982) Ultramicroscopy 8:397–402.

Primary Examiner—Kay K. Kim
Attorney, Agent, or Firm—Margaret C. Bogosian

[57] ABSTRACT

Antibody- or antibody fragment-gold cluster conjugates are shown wherein the conjugate size can be as small as 5.0 nm. Methods and reagents are disclosed in which antibodies, Fab' or F(ab')$_2$ fragments thereof are covalently bound to a stable cluster of gold atoms. The gold clusters may contain 6, 8, 9, 11, 13, 55 or 67 gold atoms in their inner core. The clusters may also contain radioactive gold. The antibody-cluster conjugates are useful in electron microscopy applications as well as in clinical applications that include imaging, diagnosis and therapy.

6 Claims, 6 Drawing Sheets

DERIVATIZED GOLD CLUSTERS AND ANTIBODY-GOLD CLUSTER CONJUGATES

This invention was made with Government support under contract number DE-AC02-76CH00016, between the U.S. Department of Energy and Associated Universities, Inc. The Government has certain rights in the invention.

CROSS REFERENCE TO RELATED APPLICATIONS

This application is a continuation-in-part application of Ser. No. 661,215 filed Feb. 27, 1991, now abandoned, which is a continuation-in-part of application Ser. No. 317,388 filed Mar. 1, 1989, and now abandoned, which is a continuation-in-part application of application Ser. No. 212,545 filed Jun. 28, 1988, and now abandoned, which is a continuation-in-part application Ser. No. 041,054, filed Apr. 22, 1987, and now abandoned.

BACKGROUND OF THE INVENTION

A number of electron dense molecules are used as contrasting agents for electron microscopy, including silver, lead, osmium, tungstates, ferritin, and colloidal gold particles. However, there are few very small ones that have site specificity. For example, labeling molecules with colloidal gold is adequate for many applications but is not precise enough to position the attachment site or control the stoichiometry of binding. Because colloidal gold attachment is noncovalent it is unstable under some conditions and because the binding to proteins is very pH dependent and requires low ionic strength, some proteins (such as IgM) are not easily labeled.

At the same time, a wide variety of antibody conjugates have been developed to be used in immunocytochemistry, in immunoassays, and in diagnostic imaging and therapy. For example, it has been shown that whole antibodies can be labeled with radioisotopes and used for the detection of cancer in humans (Burchiel et al., U.S. Pat. No. 4,311,688 and Carlsson et al., U.S. Pat. No. 4,232,119).

It has also been shown that the Fab portion of an immunoglobulin can be labeled and used in diagnostic and detection regimens [SJoquist et al., U.S. Pat. No. 3,966,898; Ling, U.S. Pat. No. 4,298,593; Aebi et al., *PNAS., USA*, 74:5514 (1977)].

It has also been shown that metal chelates can be conjugated to monoclonal antibodies and used in diagnostic and therapeutic techniques (Gansow et al., U.S. Pat. Nos. 4,454,106 and 4,472,509).

It has also been shown that electron dense moieties such as ferritin [Singer, *Nature*, 183:1523 (1959)] or colloidal gold [De Mey et al., U.S. Pat. No. 4,446,238 and Faulk et al., *Immunochemistry*, 8:1081 (1971)] can be used as markers for visualization of antibody labels in the electron microscope.

It has also been shown that immunodiffusion assay techniques can be developed using antibody-metal compound conjugates in which the metal or metal compound has a particle size of at least 5 nm (Leuvering et el., U.S. Pat. No. 4,313,734).

In the present invention, many of the drawbacks encountered by using the conventional contrasting agents for electron microscopy are overcome by using the dervatized gold clusters. These clusters are prepared by synthesizing a well-defined organometallic compound containing enough gold atoms for visibility in the electron microscope. The organic moiety may be designed to covalently attach to various groups on proteins, lipids, carbohydrates or other molecules. By using a molecular compound, the size is well defined and homogeneous. By using covalent coupling, the attachment may be performed under mild conditions without the requirement of low ionic strength. Also the resultant covalent coupling is stable under a wide range of conditions.

Further, in the present invention the derivatized gold cluster is used to prepare antibody or antibody fragment conjugates useful in diagnostic and therapeutic applications. Antibodies or active antibody fragments are covalently combined with a stable derivatized gold cluster. These clusters have an inner core of a specified number of gold atoms, for example 6, 8, 9, 11, 13, 25, 46, 55, and 67, and a shell of derivatized alkyl or aryl phosphines, preferably triaryl or trialkyl phosphines, with triphenyl phosphines being the preferred triaryl compounds, and/or mixed aryl and alkyl phosphines. The cluster also has coordinating counterions. The cluster may contain radioactive gold atoms when such activity provides diagnostic or therapeutic capabilities. These antibody-gold cluster conjugates retain the antibody specificity and activity, and are useful in any electron microscopy study, diagnostic technique, antigen localization study or therapy that relies upon the delivery of an effective dose to a targeted site.

Although each of the above-noted prior art technologies are adequate for some uses, each suffers from a deficiency now overcome by the present invention. Some of the labels noted above are generally too large for submolecular mapping in electron microscope studies. For example, an antibody molecule is about 15 nm in diameter and a colloidal gold complex is about 12–35 nm in diameter or larger (U.S. Pat. No. 4,446,238 discloses a diameter range of 20–40 nm). A conjugated label of these components is therefore about 27–50 nm in diameter; this is too large for meaningful electron microscopy studies in many fields where electron microscopy could be of value. In contrast, the antibody-gold cluster conjugates of the present invention can possess dimensions of about 5.0 nm, ideal for microscopy studies.

Some of the references noted above describe radiolabeled antibodies that are deficient because they are unable to couple more than a few radioactive elements onto an antibody without destroying the antibody activity, thus limiting the radioactive dose that can be delivered to a specific site (for imaging, diagnosis, or therapy). It is an object of the present invention to utilize a cluster system, whereby the antibody conjugate will contain multiple radionuclides, to increase the radiation dose to the targeted site. This application is of critical importance in the use of radiation to tumor therapy for certain forms of cancer. It is advantageous to deliver more radioactive dose per antibody so that the complete tumor mass receives an adequate dose. The derivatized radioactive gold cluster of the present invention can be covalently attached to specific antibody or antibody fragment sites such that the antibody or fragment carries a large number of radioactive gold atoms without significant loss of native immunospecificity. The 3.14 day half-life, 295 keV, and 66% beta emission (average range of 100 $\mu$m) of the radioactive gold ($^{199}$Au) conjugates herein described are compatible with the use of these antibody-gold cluster conjugates in cancer therapy because these properties avoid the need for extended doses of radiation to the patient while still providing an effective cytotoxic dose.

It is also an object to take advantage of the small size of the antibody-gold cluster conjugates of the present invention. For example, it is possible to more effectively and efficiently treat or detect cancer by using the advantages inherent in the small size of, for example, a Fab'-Au$_{55}$ conjugate, which permits penetration of tissues and tumors much more rapidly than previous attempts with whole antibodies coupled to radioisotopes. The small size of the conjugate also greatly improves resolution in electron microscopy studies in which specific sites or molecules or biological structures are labeled.

It is also an object of the present invention to provide a derivatized gold cluster containing enough gold atoms to be visible in the standard conventional electron microscope (CEM) and scanning electron microscope (SEM). The preferred cluster for such purposes containg 55 gold atoms. Image enhancement, using for example a silver developer, also permits the gold-55 clusters to be seen with conventional light miscroscopy for detection of cell types, tumors, viruses, and the like.

It is also an object of the present invention to provide a cluster-conjugate in which several gold clusters may be coupled to an antibody or antibody fragment. Multiple detectable atoms via a cluster enables improved signal-to-noise ratios, and therefore earlier detection of small tumors.

SUMMARY OF THE INVENTION

The derivatized gold clusters and their antibody conjugates of the present invention are a significant improvement on known compositions of materials conjugated with antibodies, antibody fragments, or other proteins. The small size of the gold cluster conjugate overcomes previous problems with size or with the inability to load more than a few atoms onto the protein. In one preferred embodiment, a Fab' fragment is covalently attached to a derivatized gold cluster containing 11 or 55 gold atoms, in which the gold may be radioactive, such that the antigenic specificity and capacity of the antibody are preserved, while at the same time, the distance of the gold cluster to the target antigen is no more than 5.0 to 6.0 nanometers (nm).

SPECIFIC DESCRIPTION OF THE INVENTION

The instant invention relates to a new class of gold cluster compounds. These clusters contain an inner core of a specified number of gold atoms wherein the number of gold atoms can be 6, 8, 9, 11, 13, 25, 46, 55 or 67. The clusters also contain an outer organic shell of derivatized triaryl or trialkyl phosphines and/or mixed aryl and alkyl phosphines. Preferred forms of the gold clusters of the present invention are: 1) the monomaleimidopropyl undecagold cluster of the formula
$Au_{11}[P(C_6H_4CONHR)_3]_7^{3+}$ where 20 R groups are $CH_3$ and one is $(CH_2)_3N(CO_2)(CH_2)$ and 2) the gold-55 cluster of the formula
$Au_{55}[P(PhCONHCH_3)_3]_{11}P(PhCONHCH_3)_2[Ph-CONH(CH_2)_3N(CO)_2(CH)_2]$, where Ph is phenyl.

These derivatfzed gold clusters have a number of useful applications. They can be used to prepare antibody-cluster conjugates. Such conjugations are useful as:

a. Probes for electron microscopy.

b. The larger clusters may be seen with conventional microscopes. Silver enhancement may also be used.

c. Probes for light microscopy. Silver enhancement may be used. Detection of cell types, tumors, viruses, etc.

c. When gold is radioactive: for diagnosis and therapy, using the antibody to direct the gold to the target. Antitumor antibodies may be used for cancer; other antibodies can be used for other applications. The larger clusters if made from high specific activity gold will deliver much more radioactive dose to target cells per antibody than using conventional methods. This should provide enhanced therapy and diagnosis. Radiogold emits radiation useful for both therapy and imaging.

d. Using non-radioactive gold for diagnosis. An x-ray source (tuned to an absorption edge being preferable) can make tumors or other antigen sites detectable by selective absorption of x-rays by the gold or by x-ray induced fluorescence of the gold. Gold may also be detected in ultrasonic imaging.

e. Dot-blot assays, or other immunoassays where proteins or other materials are adsorbed to a solid phase and gold antibodies then bound and detected by silver enhancement. Secondary antibody methods or sandwich techniques may also be used.

Gold clusters attached to proteins, lipids, viruses and other molecules:

a. These may be used for structural studies.

b. Using radioactivity, they may be used for diagnoses and therapy.

Gold clusters not attached to antibodies or proteins:

a. Water soluble forms of the gold clusters may be used for contrast enhancement of blood or other areas in x-ray imaging (CAT scans). Tailoring the organic groups around the gold greatly reduces its toxicity over other gold compounds used.

Phasing of x-ray samples:

a. By attaching these clusters to a protein crystal or ordered array or oriented fibers, a strong diffraction signal is created which may be used to phase diffraction patterns and enable solving the structure.

The present invention also relates to a method for covalently linking an antibody or antibody fragment to a stable derivatized gold cluster containing multiple atoms of gold in such a manner that the antigenic specificity and capacity of the antibody is preserved. "Cluster" as used throughout this specification, is defined as a stable group of a specified number of gold atoms, and can include clusters containing multiple radioactive gold atoms, such as $^{198}$Au and $^{199}$Au.

An undecagold complex (Au$_{11}$) was described in Safer et al., *Science*, 218:290–291 (1982) and McPartlin et al., *Chem. Comm.*, p. 334 (1969); monofunctional forms of this complex have been described in Safer et al., *J. Inorg. Biochem.*, 26:77–91 (1986) and Reardon et al., *Biochemistry*, 23:3849 (1984). The synthetic approach to the gold-11 complex used by Safer, et al. was followed here with modification to prepare the derivatized gold-11 clusters used in the present invention. This derivatized undecagold cluster is water soluble and capable of being covalently linked through the external organic shell to specific residues or molecules. As is shown below, a maleimide group on the organic shell binds covalently with a free sulfhydryl in the hinge region of Fab' or F(ab')$_2$ fragments or to reduced disulfide groups in whole IgG molecules.

The preparation of the derivatized gold cluster of the present invention is a multi-step procedure that is outlined in the following scheme:

wherein
  $n=6, 8, 9, 11, 13, 25, 46, 55$ or $67$;
  X is a counterion such as a halogen ion, preferably chlorine;
  m = the appropriate fixed number of phosphines surrounding the gold core; and
  p+q always equals m.

The number of phosphines that surround the gold core will be determined by the number of gold atoms in the core. The number of gold atoms in the core will dictate the binding angles and chemical binding constants of the core and will thus determine the number of phosphine groups that can bind with the core. For example, when the gold core contains 11 gold atoms, m=7, that is seven phosphine groups surround the core; when n=13, m=10; and when n=55, m=12.

In an alternate synthetic approach, steps 1 and 2 depicted above can be bypassed by using derivatized phosphines directly in the formation of the cluster.

The antibody or antibody fragment used in this invention may be any polyclonal or monoclonal antibody or antibody fragment which forms an immunochemical reaction with an antigen. "Antigen" therefore is a term of art denoting any substance or molecule which induces the formation of an antibody (i.e., that can trigger an immune response), and can be a virus, a bacterium, a fungus, a parasite, tissues or cells not naturally a member of a hosts family of tissues or cells, or even a portion or product of any of these organisms. "Antigenic" or immunogenic" are used to describe the capacity of a given substance to stimulate the production of antibodies. "Antibody" is a term of art denoting the soluble substance or molecule secreted or produced by an animal in response to an antigen, and which has the particular property of combining specifically with the antigen which induced its formation. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds). When IgG is treated with the enzyme papain, an antigen binding fragment can be isolated, termed Fab. When IgG is treated with pepsin (another proteolytic enzyme), a larger fragment is produced, F(ab')$_2$. This fragment can be split in half by reduction to Fab'. The Fab' fragment is slightly larger than the Fab and contains one or more free sulfhydryls from the hinge region (which are not found in the smaller Fab fragment). The term "antibody fragment" is used herein to define both the Fab' and F(ab')$_2$ portions of the antibody. It is well known in the art to treat antibody molecules with pepsin in order to produce antibody fragments [Gorevic et al., *Methods of Enzyol.*, 116:3 (1985)].

The term "immunochemical reaction" is used to denote the specific interaction which occurs between an antigen and its corresponding antibody. Methods for obtaining antibodies have been extensively discussed and are well-known in the art. A useful reference for obtaining monoclonal antibodies is Koprowski et al., U.S. Pat. No. 4,196,265. The selection of the antibody for the practice of this invention will depend upon the end use for which the antibody-gold cluster conjugate will be employed. Such selection is within the skill in the art.

Of particular importance to the present invention is the size of the antibody or antibody fragment molecules. The antibody molecule is about 15 nm in diameter and the Fab' fragment is about 5.0 by 4.0 by 3.0 nm (about 50 kD). This size makes the antibody label 1/5 to 1/10 the size of the colloidal gold antibody labels synthesized according to the prior art. This smaller size also permits the use of the label for discerning specific sites on single protein molecules or nucleic acid chains, and also permits the labeling of secluded sites previously inaccessible by larger labels, a quality particularly useful in electron microscopy.

The antibody-gold cluster conjugates of the present invention show numerous advantages over prior art materials. The binding of the derivatized gold cluster to the antibody or antibody fragment is to a crystallographically known specific site, and for the Fab' and F(ab')$_2$ fragments, the cluster is located at a maximal distance from the antigen-combining site, thereby minimizing any effect on antibody immunoreactivity as a result of conjugation. In addition, when the radioactive gold cluster is used, because the binding of the radionuclide is covalent, the bonds are stable, minimizing the chance of exchange or displacement of the radionuclide.

Figure 1:
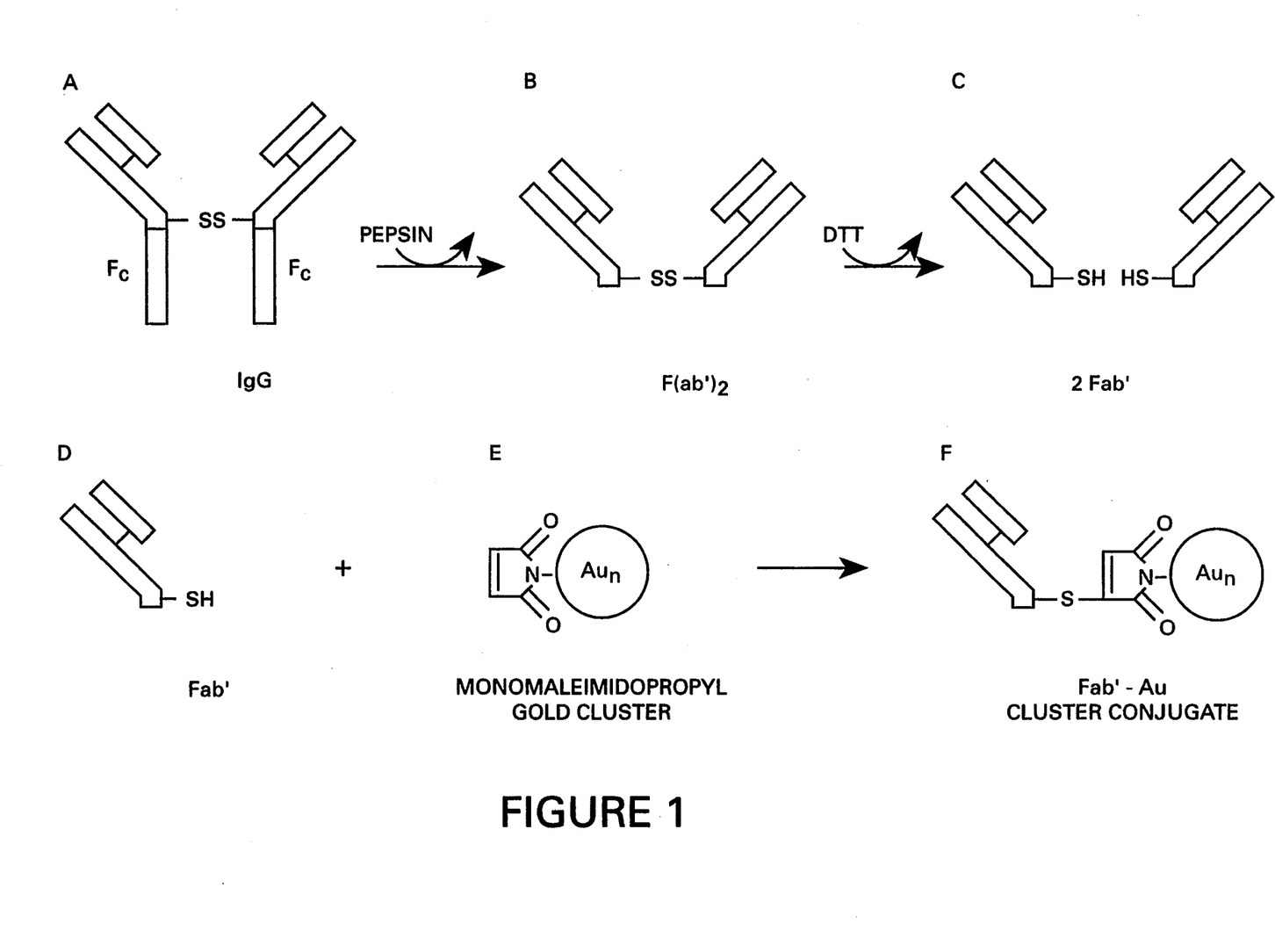
FIG. 1 shows a reaction scheme for labeling a Fab' fragment with a derivatized gold cluster of the present invention.
Figure 2:
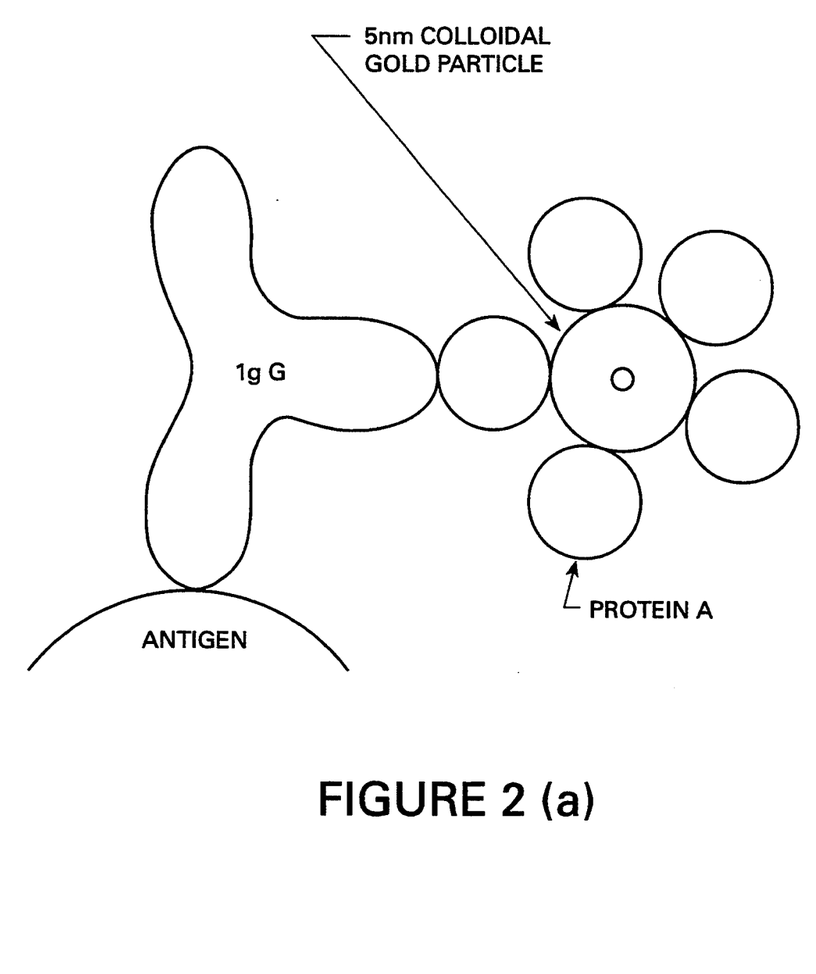
FIG. 2 shows the size comparison of antibody labels used in electron microscopy. A commonly used conventional label (A) relies on staphylococcal protein A binding to the Fc region of an immunoglobulin; the overall dimension is 25 nm or greater. A label of the present invention (B), the undecagold cluster bound to a Fab' fragment, is no more than 5.0 to 6.0 nm.

The rabbit IgG described in the examples has only one disulfide in the hinge region of the antibody (see FIG. 1). Human antibodies have between 2 and 15 disulfides in the hinge region, most of which remain after pepsin digestion (see Gorevic et al., cited above). These human antibody fragments drastically increase the capability of loading clusters onto the antibody label, which should make the fragments easily visible in thin sections or conventional electron micrographs without the sacrifice of the high resolution of this technique. The labeling procedure of the present invention is generally applicable to a broad range of antibodies and antibody fragments.

The antibodies are generally maintained in an aqueous solution that contains an ionic compound. A physiologic normal saline is preferred. Other ionic solutions, such as those containing sodium or potassium phosphate, sodium carbonate and the like, are known in the art and may also be used in the practice of this invention.

It is known in the art that Fab' fragments can be prepared that have one free sulfhydryl group at a location distant from the antibody-antigen binding region. See Martin et. al., *Biochemistry*, 20:4229 (1981). Such antibody fragments can be coupled to the undecagold cluster and still retain full antigenic specificity and capacity.

The synthesis of the antibody-cluster conjugates of the present invention is illustrated, for example, by the formation of the antibody fragment (Fab')-undecagold cluster shown in FIG. 1. First, IgG molecules are digested with the enzyme pepsin to form $F(ab')_2$. This fragment is reduced with a suitable reducing agent such as dithiothreitol (DTT) to form Fab' fragments. Treatment with DTT in this manner exposes a specific thiol (—SH) to which the activated gold cluster is bound.

Another method of forming antibody-gold cluster conjugates involves oxidation of the carbohydrates on the IgG molecules with periodate to form aldehyde groups, adding clusters containing free amines, and finally, stabilizing the Schiff's bases thus formed using borohydride. The result is a cluster cross-linked through the carbohydrate moiety on the IgG molecule.

Another method of forming whole antibody-cluster conjugates involves reduction of IgG with DTT, forming relatively short-lived free sulfhydryls. DTT is removed by column chromatography and the free sulfhydryls reacted quickly with appropriate gold clusters.

To preserve the maximum biological activity of the antibody, the use of strong acids or bases to adjust pH should be avoided (strong acid or base causes localized denaturation in the solution). The pH is preferably controlled by including a suitable buffer in the aqueous solution containing the antibody. For example, $NaHCO_3$ is known in the art and may be employed in the practice of this invention. The choice of the appropriate buffer is within the skill of the art.

As has been described above, this invention may take many forms, all dependent upon the end use of the antibody-cluster conjugate. For example, the Fab'-$Au_{11}$, Fab'-$Au_{13}$ and Fab'-$Au_{55}$ conjugates are useful for diagnosing and treating cancer—using an anti-tumor antibody and a radioactive gold cluster, the conjugate selectively binds to the tumor cells reactive with the Fab' fragment. Concurrently, the radioactive gold atoms decay with emission of a gamma ray, thus permitting imaging of the tumor. The $Au_{11}$, $Au_{13}$ or $Au_{55}$ cluster conjugated to 17-1A monoclonal antibody is useful for the detection of human colon carcinoma. Also, decay of the radioactive gold cluster produces beta particles in an energy range suitable for killing surrounding tumor cells within a small, several cell radius. Using these clusters, therefore, enough radioactive dose may be delivered to treat cancers while limiting extended doses of radiation to the patient.

When the antibody-gold cluster conjugate is being used for microscopy purposes or nuclear medicine, the gold cluster labeled antibodies can be enhanced for easier detection by a silver reaction. This produces a controlled size silver particle around each cluster that can be seen, for example, in the electron microscope and light microscope, depending on the size and number of particles. The antibody-gold cluster conjugates enhanced by a silver reaction have advantages over antibodies labeled with conventional labels. The gold cluster and its attachment to antibodies is very stable and not affected by extremes in pH or ionic strength as are many other labels. It has a longer shelf life and is useable under more conditions. Equally important, its preparation and use are simple and reliable.

The antibody-gold cluster conjugates of the present invention, enhanced by a silver reaction, have a variety of applications, including diagnostic medicine, electron microscope studies, and light microscope studies. Any antibody testing could be accomplished with this improved product, such as testing for AIDS or any other vital or bacterial presence. A simple "dipstick" test based on this technology could be used. Here the antigen to be detected is bound to a solid phase material on a stick, which is then inserted into the antibody-cluster solution. If antigen is present, antibody and cluster will bind to it. After rinsing, a color is developed from the gold.

The silver enhanced conjugates are also useful in electron microscopy because of the small size of the Fab'-gold cluster conjugate (5–10 times smaller than other antibody labels), which permits this reagent to diffuse into tissues and samples better and to label at a higher resolution. Subsequent enlargement of the gold by silver makes visualization straightforward. Also the poor stability of conventional antibody labels makes them unuseable in some cases. The antibody-gold cluster labels have superior stability properties.

Silver exists in an oxidized state in many compounds. Gold can catalyze the reduction of silver ions to silver metal, $Ag°$, which precipitates out around the gold. In the present invention, the gold cluster serves as a reaction site for silver deposition. The initial grains grow with time until they can be seen easily with an electron or light microscope. The gold cluster serves as a nucleation site for specific silver deposition.

When the antibody-gold cluster conjugates of the present invention are used in electron microscopy (EM), the significantly smaller size of the conjugates of the present invention greatly improves the resolution of EM studies in which specific sites or molecules or biological structures are labeled, thus permitting or enhancing domainal mapping of single molecules or pinpointing specific molecules, sites or sequences in supramolecular complexes.

When used for clinical purposes, such as imaging or radiotherapy, the antibody-gold cluster conjugates of this invention may be administered in vivo in any pharmaceutically suitable carrier. As noted above, a physiologic normal saline solution can be used, and may optionally include an appropriate amount of carrier protein such as human serum albumin (for antibody stabilization). The appropriate concentration of any biologically active material in a carrier is routinely determined by practitioners in the art.

EXAMPLE 1

Preparation of Monomaleimidopropyl Gold-11 Cluster

The monomaleimidopropyl gold-11 cluster (hereinafter referred to an undecagold cluster) is prepared as follows: A solution of tolyl magnesium bromide is cooled to 0° C. and 45 g of phosphorous trichloride is added. The mixture is refluxed for 7 hrs at 90°, cooled, and then poured into 1.4 kg of ice and 90 ml of concentrated HCl. The mixture is extracted with benzene, dried and recrystallized in 95% ethanol. Tris-p-tolylphosphine ts produced.

42 g of tris-p-tolylphosphine is then suspended in 150 ml of pyridine and heated to 40°, to which 66 g of $Na_2CO_3$ in 500 ml of water is added. The phosphine is oxidized by adding 10 g of $KMnO_4$. After heating to 125°, 200 g $KMnO_4$ is added. The pyridine is removed by distillation and the product filtered through Celite. The filtrate is cooled to 0° and adjusted to pH 1 with concentrated HCl and the precipitate collected by filtration and washed with cold water. Tris-p-carboxyphenylphosphine oxide is produced.

37 g of tris-p-carboxyphenylphosphine oxide is mixed with 15 ml of acetyl chloride and 500 ml methanol and heated to 50° overnight. The methanol is evaporated and the product purified by adding 400 ml of boiling benzene, cooling, and then adding 800 ml of petroleum ether. The product, tris-p-carbomethoxyphenylphosphine oxide, is collected by filtration.

32 g of tris-p-carbomethoxyphenylphosphine oxide is placed in 300 ml of benzene and 28 g of trichlorosilane and heated to 90° for 5 hr. The solvent is removed and the residue dissolved in 300 ml of benzene and then 150 ml of 28% $NH_4OH$ is added. The solid is filter collected and dried and is tris-p-carbomethoxyphenylphosphine.

25 g of tris-p-carbomethoxyphenylphosphine is added to 32 g of KOH in 200 ml of water and 200 ml of methanol and refluxed for 5 hr. The cooled solution is adjusted to pH 1 with 25% HCl and the precipitate collected by filtering and washed with water. Tris-p-carboxyphenylphosphine is produced.

0.8 g of tris-p-carboxyphenylphosphine is dissolved in 20 ml of dimethylformamtde (DMF) and is mixed with 2 g of 1,1-carbonyl diimidazole. After 1 hr 60 m moles of methylamine in 13 ml of DMF and 220 mg of 1,3-diaminopropane are added. After 90 min the solvent is removed and 30 ml of methanol and cold 0.5% $Na_2CO_3$ in 300 ml water are added. The precipitate is filtered, washed with water, and dried. It is mostly a mixture of 6 parts of tris-p-N-methylcarboxamidophenylphosphine and 1 part p-N-aminopropylcarboxamidophenyl-di-p-N-methylcarboxamidophenylphosphine.

This mixture is the one used to prepare the gold cluster since the cluster has 7 phosphines surrounding the 11 gold atom core, and statistically the predominant product should therefore have 6 phosphines of the tris product and 1 of the N-aminopropyl product giving only one terminal amine, making it monofunctional. This amine is later converted into a maleimide group which reacts with sulfhydryl groups. Some percentage of clusters will have other ratios of the tris and N-aminopropyl products, but these can be removed during the purification.

0.14 moles of the phosphine mixture in 3 ml methanol is mixed with an equimolar amount of AuCN in 5 ml 100% ethanol and stirred for 30 min. An equimolar amount of a 0.1% ethanolic solution of $NaBH_4$ is slowly added over 2 hr. The undecagold cluster is formed and has a reddish-brown color. Eight drops of acetone are added to quench any excess borohydride. To improve its solubility in aqueous buffers, the cyanide is exchanged with the chloride counterion by mixing with 8 ml of water and 3 g of Dowex (chloride form) overnight then filtering off the ion exchange resin. The yield of cluster is typically 30%, which for this case produces 3.9 moles.

EXAMPLE 2

Purification of the Undecagold Cluster

Once successful clusterification has been achieved, the reaction mixture contains the cluster, excess phosphines, and gold phosphines in a solvent of methanol/ethanol/water. The undecagold cluster must be separated out. Also several uudecagold species are produced, some that are nonfunctional (no amines), some that are monofunctional (1 amine), as well as small amounts of difunctional, trifunctional, etc. The monofunctional form should be isolated.

The first step is to purify the clusters from the general reaction mixture. This may be done by size exclusion chromatography since the undecagold cluster has a mol wt. of approx. 5000, and the phosphines are approx. 250. Safer et al. (1986) cited above describe the use of a 2.5×100 cm column of BioRad P-10 running in 0.6M triethylammonium bicarbonate and 5% methanol. The triethylammonium bicarbonate buffer is prepared by bubbling $CO_2$ into a mixture of 1 part triethylamine and 5 parts water for about a day to make 1.2M triethylammonium bicarbonate. This is diluted and methanol added to form the above buffer. The advantage of this buffer is that it is volatile and can be removed fairly easily by rotary evaporation. However, 0.5M NaCl is another suitable buffer choice (buffered by 0.1M Tris - HCl, pH 7) for this column. P-10 has a fractionatton range to 15,000 mol. wt., so that colloids or larger aggregates may be removed. The disadvantage of this column is its 6–8 hr run time. For most runs, little material larger than undecagold is formed and therefore another material with faster flow properties can be used such as the Amicon desalting gel GH25 which has a mol. wt. cutoff of 3,000. The cluster comes through in the void volume but runs are shortened to 30 min to 1 hr due to its faster flow rate under pressure.

The gold cluster peak from the column is pooled. For some columns the cluster peak may somewhat overlap with the phosphine/gold phosphine peak. To determine which fractions to pool, a UV/visible spectrum is taken (from 200 to 600 nm and the 280/420 absorption ratio may be used as a guide to cluster purity. The undecagold has a ratio of 3.6 ($E_{420}=4.71\times10^4$), whereas the phosphine components absorb only in the UV region (280) but not at 400. A 280/420 ratio greater than 3.6 indicates an impure cluster.

The pooled pure peak is next dried by rotary evaporation. Care must be used due to the large flakes formed by the triethylamine. The residue is rinsed with 5 ml of methanol and reevaporated four times at 45° C. to remove most of the buffer.

Due to the mixture of phosphines used to form the cluster, a statistical mixture of clusters is produced, the monofunctional form being the one desired. Ion exchange chromatography is used to isolate this form. The column used is a 1×50 cm CM-Sepharose Fast Flow (Pharmacia) run in a gradient with A=water and B=0.25M NaCl, 10 mM triethylammonium-HCl (pH 7.0) and 5% methanol. The gold cluster sample is dissolved in a 5% methanol-water solution for injection and the gradient is run from 0–100% B. Bands of yellow colored gold cluster will separate; the first band to come off is the non-functional cluster, next is the monofunctional cluster desired, with one amine.

Next, the purified cluster must be desalted. This may be accomplished by dialysis using 3,000 mol. wt. cutoff dialysis tubing (Spectrapor) or by binding the cluster in the salt buffer from the previous column to a reverse phase biphenyl silica column (Vydac 219), rinsing with distilled water to remove the salt, and eluting with 0.3M treithylammonium bicarbonate buffer in 70% methanol. The buffer is removed by rotary evaporation, as described above. The cluster is brought up in methanol at a concentration of 5 nmol/μl and stored in the refrigerator.

EXAMPLE 3

Activation of Undecagold Cluster

The reactive maleimide group is attached to the single amine of the cluster immediately prior to use. The reason for this attachment is that maleimides have only a few hours half-life in aqueous solutions. The recovery of gold through this step is 50–80% and the gold cluster is mixed with the antibody in 5–10 fold molar excess, so an appropriate amount is pipetted out of the methanol stock solution. For example, 200 μg of Fab' (mol. wt. 50,000) is 4 nmol, so 50 nmol of $Au_{11}$ (for a 10:1 ratio) should be used.

Figure 3:
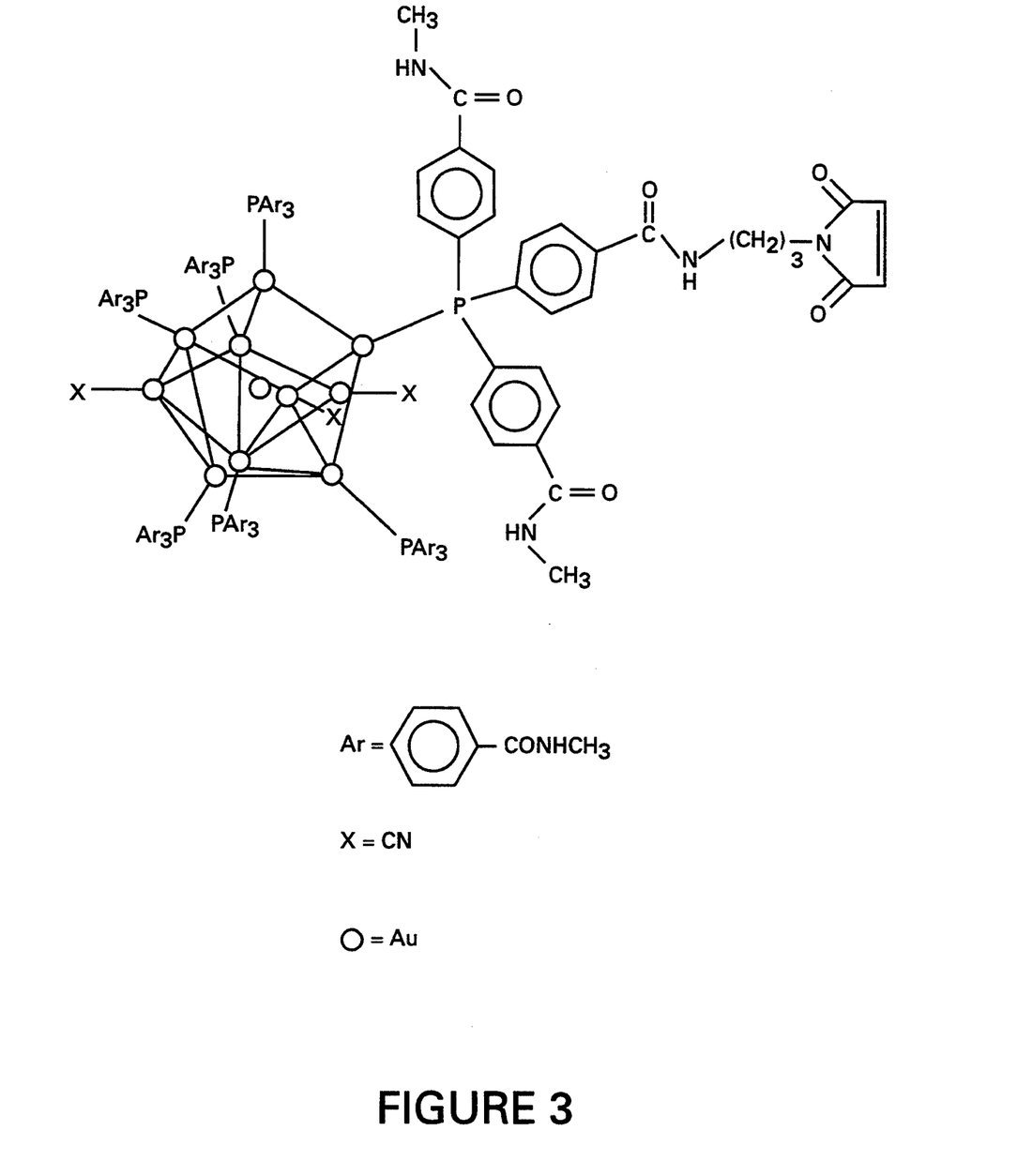
FIG. 3 shows the undecagold cluster consisting of a core of 11 gold atoms with an organic shell, and an overall diameter of 2.0 nm.
Figure 4:
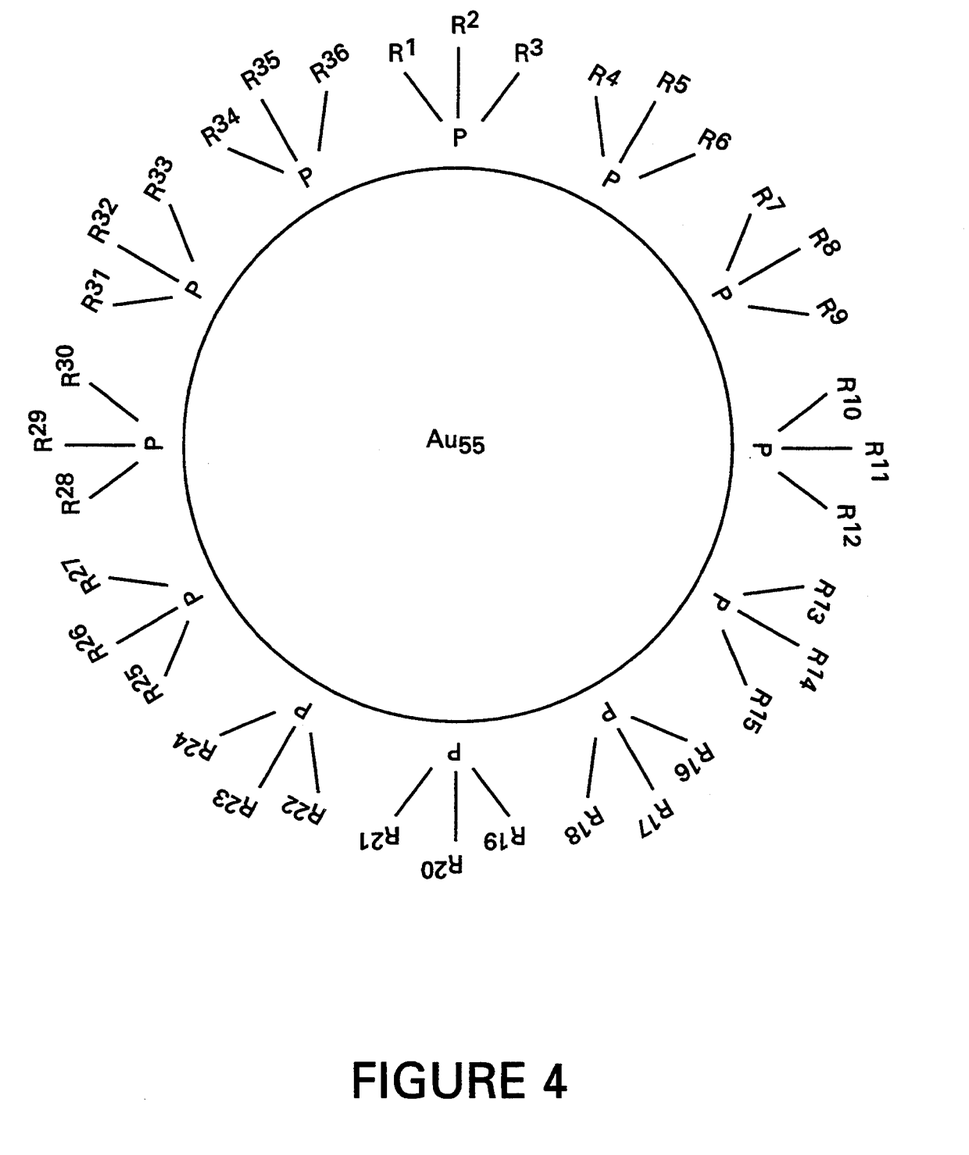
FIG. 4 shows the gold-55 cluster consisting of a core of 55 gold atoms which is 1.4 nm in diameter with an organic shell of 12 derivatized triphenylphosphines with an overall dimension of 2.7 nm.
Figure 5:
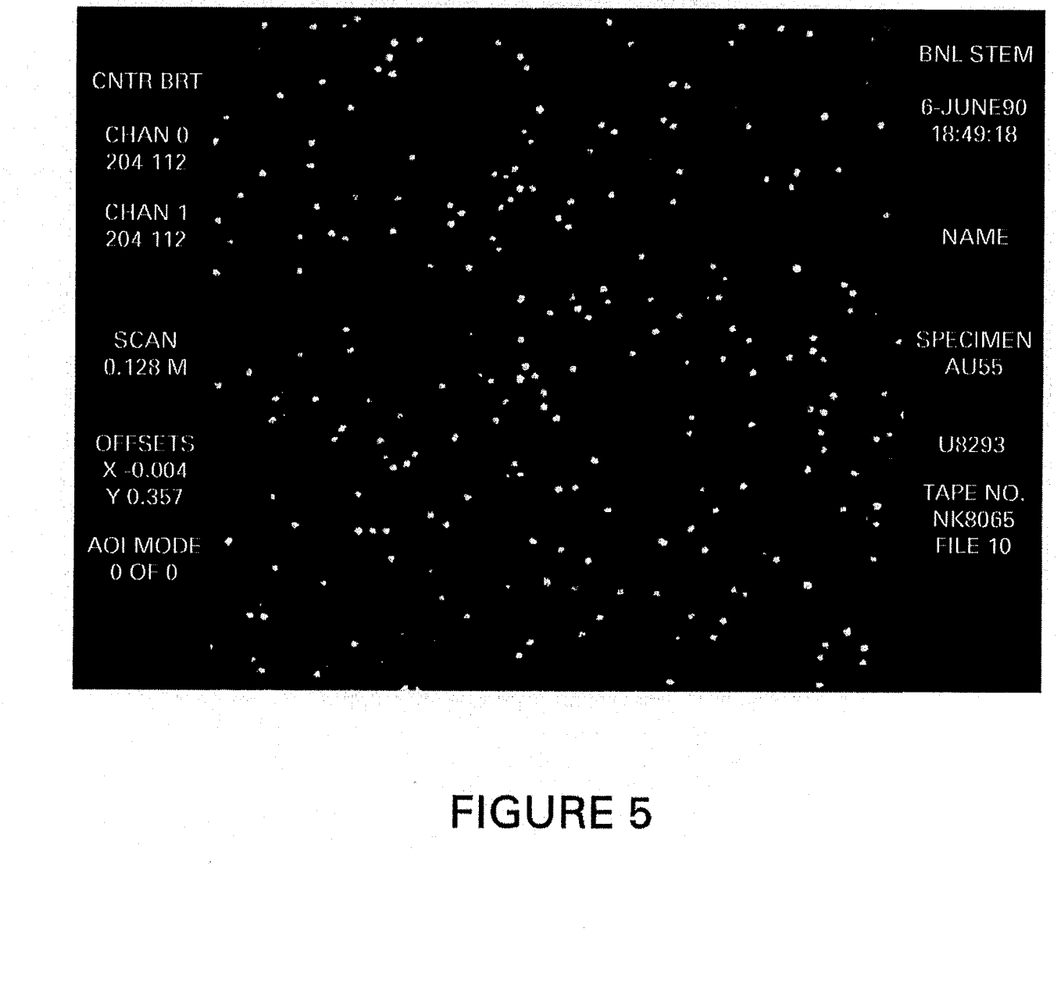
FIG. 5 is an electron micrograph using the Scanning Transmission Electron Microscope (STEM) of the gold-55 cluster of the present invention.
Figure 6:
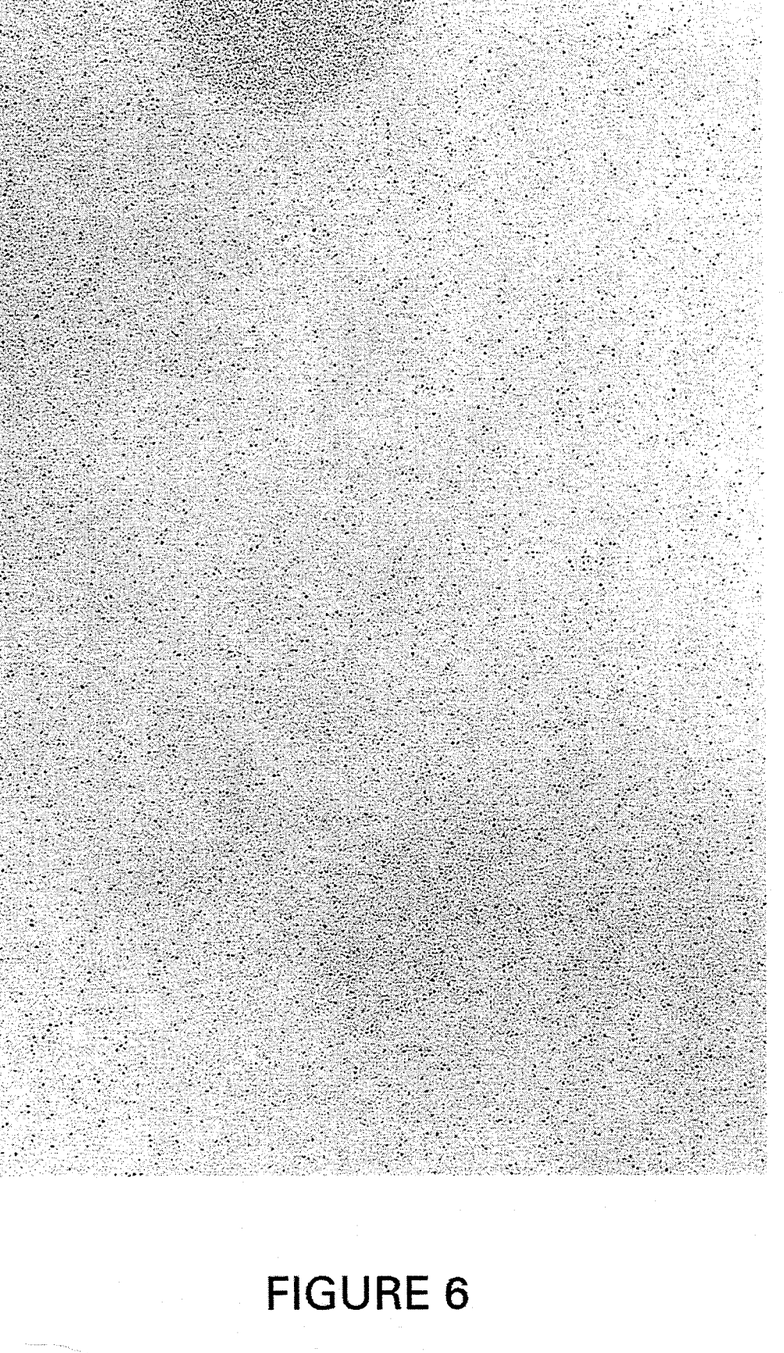
FIG. 6 is an electron micrograph using the CEM of the gold-55 cluster of the present invention.

50 nmol of $Au_{11}$ in 10 μl of methanol is mixed with 1 mg of N-methoxycarboxyl maleimide (NMCM) and 10 μl of a 0.5M $NaHCO_3$ solution on ice for 20 min. The reaction is diluted with 1 ml of distilled water and applied to a 3 ml gravity fed ion exchange column, CM-Sepaharose C50, which has been cycled with distilled water, 0.1M phosphate buffer (pH 7) and distilled water. The undecagold adheres to the top of this column and the excess NMCM removed by washing with 9 ml of distilled water. The $Au_{11}$ is eluted, using a 0.1M Na phosphate (pH 7.0 buffer). The gold fractions are combined and quantitated using a spectrophotometer set at 420 nm and the extinction coefficient $E_{420}=4.71 \times 10^4$. The compound produced is the monomaleimide undecagold cluster shown in FIG. 3.

EXAMPLE 4

The reaction scheme shown in FIG. 1 is used for labeling Fab' with the undecagold cluster. Rabbit IgG (from Cooper Biomedical, Inc.) was digested with pepsin to yield $F(ab')_2$ fragments joined by a disulfide (A,B). The constant fragment ($F_c$) regions were removed by a Staph A-Sepharose column; other digested fragments were removed on a high-pressure liquid chromatography (HPLC) Fractogel TSK HW-55 (S) column. Next, 20 mM dithiothreitol (DTT) was used to reduce the disulfide link (B,C), which produced the Fab' fragment (2 hour reaction time under $N_2$). DTT was removed with the HPLC column. Between runs through the column, protein was concentrated to 0.5 to 1.0 mg/ml with Amicon Centricon 10 microconcentrators. Undecagold was activated immediately prior to use by reaction of monoaminopropyl-$Au_{11}$ and N-methoxycarboxyl maleimide to form monomaleimidopropyl-$Au_{11}$ (E). The product was purified on a carboxylic CM Sepahrose column. The Fab' and activated $Au_{11}$ were incubated overnight at 4° C. (D-F). Unreacted $Au_{11}$ was removed with an HPLC Fractogel TSK HW-40(S) column.

EXAMPLE 5

In the undecagold-labeled Fab' fragments produced according to Example 4, the Fab molecules show in scanning transmission electron microscope images quantitative labeling—the undecagold spots (0.8 nm diameter) are at one end of these 50 kD fragments. Some Fab' fragments show more than one $Au_{11}$ cluster attached. Each Fab' fragment binds usually one undecagold cluster, but sometimes two or three (and rarely four). Gold clusters on 724 Fab' molecules were counted to determine a more exact stoichiometry. The mean was found to be 1.5±0.7 (S.D.) clusters per Fab'. A spectral assay of the Fab'-$Au_{11}$ complex in solution indicated a stoichiometric ratio of 1.4 $Au_{11}$ to 1Fab'. The undecagold cluster on the Fab' was located in the same place on each Fab' molecule (at one end), as expected from the position of the free sulfhydryl group. When two undecagold clusters were found on a Fab' fragment, the second site was always 1.8 to 2.8 nm from the first, which again indicated specific attachment. Similarly, when a third undecagold cluster was present, it was 1.8 to 2.8 nm from the first; the three clusters usually formed a triangular cap (sometimes they formed a linear array) on one end of the Fab' molecule. The undecagold clusters were always localized at one end of the Fab' molecule. Some of these multiply labeled Fab' fragments csn be identified when they are bound to the antigen and therefore do not appear to affect antibody activity.

EXAMPLE 6

Following the synthetic approach depicted in FIG. 1 and exemplified in Example 4, the following antibodies can be labeled with the derivatized gold clusters of the present invention:

1. 17-1A mouse monoclonal against human colon carcinoma
2. H2-4B5 mouse monoclonal, anti-influenza
3. BR 55 mouse monoclonal anti-human breast tumor
4. Human IgM
5. rabbit anti-ferritin
6. Rabbit anti-22S dynein
7. Rabbit anti-14S dynein
8. Rabbit anti-flagellin
9. Rabbit anti-bovine serum albumin
10. Rabbit anti-human
11. mouse monoclonals to bovine factor V
12. Rabbit anti-gene product 7 (T4 bacteriophage)
13. Rabbit anti-gene product 8 (T4)
14. Rabbit anti-gene product 10 (T4)
15. Goat anti-mouse
16. Goat anti-rabbit
17. Rabbit anti-goat

EXAMPLE 7

Preparation of Radioactive Undecagold Cluster 8 mg of pure gold was irradiated at the Brookhaven National Laboratory (BNL) High Flux Beam Reactor (HFBR) for 2 hours. While this does not produce carrier free [199]Au, it is a convenient method to yield the levels of specific radioactivity necessary for preliminary tests. Irradiation of enriched [198]Pt is one method to yield highly pure [199]Au (after separation). The double neutron capture on natural gold employed in fact yielded both [199]Au and [198]Au. The irradiated gold was then dissolved in 5 drops of aqua regia. It was stirred with mild heating (80° C.) until dissolved. Next it was taken to dryness with heat. 5 drops of concentrated HCl was added dropwise and the solution again heated to dryness in order to drive off the nitric acid. The material was dissolved in 5 ml of water to make chloroauric acid (HAuCl$_4$). This was then converted by reduction to AuCN.

The gold cyanide recovered was suspended in 3 ml of absolute ethanol. Two substituted triphenyl phosphines (PPhR$_3$,Ph=phenyl) were synthesized. One of the organic groups, R', contained a propylamine (R'=—CO—NH(CH$_2$)$_3$—NH$_2$), whereas the other was R=CO—NH—CH$_3$. A 20 to 1 proportion of R to R' yields a predominantly monofunctional eleven gold atom cluster, Au$_{11}$ (PPhR$_3$)$_6$PPhR$_2$R'.

These phosphines were prepared as follows: First tolyl magnesium bromide was synthesized by reacting p-bromotoluene with magnesium metal in tetrahydrofuran. This Grignard reagent was reacted with phosphorous trichloride in tetrahydrofuran with refluxing. The product was tris-p-tolyphosphine. After crystallization, this material was treated with sodium carbonate and potassium permanganate in water to yield tris-p-carboxyphenylphosphine oxide. Treatment of this with methanolic hydrochloric acid yielded tris-p-carbomethoxyphenylphosphine oxide. Trichlorosilane in benzene converted this to tris-p-carbomethoxyphenylphosphine. A solution of potassium hydroxide in 1:1 methanol water was added. After refluxing, tris-p-carboxyphenylphosphine was isolated. This product was reacted with 1,1-carboxyl dimidazole. Methylamine and 1,3-diaminopropane were mixed in a 20:1 proportion in dimethylformamide. This was added to the above material and a mixture of mostly 6 parts tris-p-N-methyl-carboxamidophenylphosphine and one part 4-N-(-aminoalkyl)carboxamidophenyl-di(4-N-methylcarboxamidophenyl) phosphine was produced.

A stoichiometric amount of this 6:1 mixture of phosphines, 16 mg, was dissolved in 2 ml of methanol, which was added to the AuCN suspension. With stirring, 0.4 ml of a 0.1M ethanolic solution of sodium borohydride was slowly added. Afterwards, a fewdrops of acetone were used to quench any excess borohydride.

The reaction mixture was next taken to dryness in vacuo and redissolved in 2.5 ml of water and 2.5 ml of methanol. 1.5 g of Dowex I (chloride form) was added and allowed to react overnight. After filtering, the Au$_{11}$ clusters were separated from other reactants by passage through a Sephadex G25 column equilibrated in 0.6M triethylammonium bicarbonate buffer containing 5% methanol. The appropriate peak fraction was dried in vacuo. At this point a CM-Sepharose ion exchange column was sometimes employed to purify further the clusters to obtain only the monofunctionalized specie.

The single primary amine on the Au$_{11}$ cluster was next converted into an N-alkylmaleimide which would react specifically with free sulfhydryl groups. This was done by reacting the above described cluster with N-methoxycarboxyl maleimide and isolating the product on a CM Sepharose column. The resultant monomaleimidopropyl gold clusters were then ready for labeling the appropriately prepared antibodies.

EXAMPLE 8

17-1A monoclonal antibodies, which were reactive toward human colon carcinoma, were treated in two ways for labeling. One method was used to label whole IgG molecules; the other was to label the smaller Fab' antibody fragments. These two species have different molecular weights and have the gold label at possibly different sites. Consequently, their biodistribution in an animal after injection, blood clearance times, and tumor/non-tumor localization ratio will be different. This latitude in properties will provide some optimization when choosing a preparation for diagnosis or therapy.

The IgG labeling was accomplished as follows: An aliquot of 17-1A IgG was treated with dithiothreitol (DTT, final concentration 20 mM) for an hour at room temperature, to transiently reduce some disulfides. Next, DTT was removed with a Sephadex G25 column equilibrated in 10 mM sodium phosphate buffer, pH 7.0. A 5-fold molar excess of monomaleimidopropyl gold cluster was added and allowed to react at 4° C. overnight. The excess unreacted gold cluster was removed by multiple washings on an Amicon Centricoh-30 filter or passage down a DuPont GF 250 gel exclusion column equilibrated with 0.2M sodium phosphate buffer, pH 7.0.

The Fab' labeling was done similarly: 17-1A IgG was digested with pepsin overnight to yield F(ab')$_2$ fragments which were purified on a DuPont GF250 HPLC column. The F(ab')$_2$ material was reduced to Fab' with 20 mM DTT for 1 hour at room temperature. Successive steps in gold labeling were identical to the above IgG labeling description.

A typical stoichiometry of the labeling was 1:1 for the Fab' (one Au cluster on each Fab' molecule) and 2 Au clusters per whole IgG molecule.

EXAMPLE 9

Preparation of Gold Cluster-F(ab')$_2$ Antibody Fragment Conjugates

F(ab')$_2$ antibody fragments generally have different binding constants than Fab' or IgG, penetrate tissues more rapidly than IgG (due to their smaller size), have different tissue distributions when injected from Fab or IgG and clear from organs at a different rate. They also have no Fc region and binding to cells with Fc receptors is therefore eliminated. For one or more of these reasons, labeled F(ab')$_2$ may be the preferred fragment to use in a given case. Two methods can be used to gold cluster label F(ab')$_2$ antibody fragments:

Method 1: A different undecagold cluster was prepared from that described in Example 1 above. Instead of monomaleimido undecagold which has only one reactive site for linking to the antibody, dimaleimido undecagold was prepared which has two antibody binding sites. Fab' antibody fragments were prepared from F(ab')$_2$ as described above. These were incubated with the dimaleimido undecagold clusters. Two Fab' fragments react with one gold cluster and form an F(ab')$_2$ fragment with a gold cluster in the middle.

Method 2: An antibody is chosen that has more than one sulfhydryl in its hinge region. Many human antibodies have mote than one and many mouse monoclonal antibodies have three. Fab' fragments are prepared by standard methods and allowed to react with the monomaleimido undecagold cluster. The gold will react with one sulfhydryl on the Fab', but this fragment has an additional free sulfhydryl(s) that can recombine with another Fab' fragment. One of the major products formed is F(ab')$_2$-Au$_{11}$ which is then separated chromatographically from Fab'-Au$_{11}$ or other products.

Both of these methods were used to prepare F(ab')$_2$-Au$_{11}$ conjugates using 17-1A mouse monoclonal antibody which is specific for human colorectal tumors. After preparation, this labeled antibody was tested to find if its immunoreactivity had been altered. A radioimmunoassay was performed using cell binding to cultured human colon carcinoma cells and to melanoma cells (the control). There was no binding to the control cells and the labeled F(ab')$_2$ had virtually identical binding to the tumor cells as did native unlabeled F(ab')$_2$.

EXAMPLE 10

The IgG used was rabbit anti-horse ferritin. To demonstrate that the gold-labeled Fab' fragments retained their antibody activity, they were mixed in 20-fold molar excess with horse ferritin; each ferritin molecule has a shell of 24 similar subunits that encapsulate the 8.0-nm diameter core of iron oxides. After a 1-hour incubation, any unbound material was eliminated by passage through a TSK-HW55(S) HPLC column.

Scanning transmission electron microscope images of ferritin molecules with Fab'-Au$_{11}$ molecules bound were taken. In these images, the maximum distance of the gold clusters from the edge of the ferritin molecules is 5.0 nm; some clusters are much closer. The number of Au$_{11}$ clusters that could be counted per ferritin molecule was 7.3+3.8 S.D. (207 molecules examined) and varied from 0 to 21. Note that ferritin is normally used as an EM label, but with this technique it is labeled with a marker whose electron dense core is 1/10 the size of the ferritin core.

EXAMPLE 11

Labeling IgM with Gold Clusters

The motivation for labeling other antibody isotypes includes several considerations: a) Each Isotype will have a different biodistribution and may be useful in diagnostic targeting, b) Human antitumor monoclonals are only available currently as IgM, c) Because IgM is a polymer of five IgG-like molecules, it should be possible to load each IgM with perhaps up to five times the gold label than on an IgG molecule. This may deliver more gold to the intended target and improve diagnostic or therapeutic effects.

0.3 mg of human IgM was treated with 40 mM dithtothreitol (DTT) in 10 mM sodium phosphate buffer pH 7.0 for 1 hr at room temperature. The mixture was applied to a 1×25 cm G25 column running in 10 mM phosphate buffer, pH$_7$ to remove the DTT. The IgM recovered was incubated with a 14 fold molar excess of the monomaleimido undecagold cluster overnight at 4° C. in 0.1M sodium phosphate buffer, pH 7.0. The material was then concentrated using an Amicon Centricon 30 filtration device and applied to a Dupont Zorbax GF-250 gel filtration column running in 0.2M phosphate buffer pH 7.0 to remove unbound gold clusters. Four major protein peaks eluted corresponding to intact and reduced forms of IgM. The intact IgM peak was labeled with 8.5 gold clusters as determined by spectrophotometry and scanning transmission electron microscopy.

EXAMPLE 12

Silver Enhancement of Undecagold Cluster Labeled Antibodies

The undecagold cluster is only approx. 2.0 nm in diameter, and its dense core of eleven gold atoms is only 0.82 nm across, which is only about four atoms wide. Although this cluster is easily seen in some high performance microscopes (e.g., the high resolution scanning transmission electron microscope, STEM) it is difficult to observe in most commercial electron microscopes. Needless to say it is invisible in the light microscope, except in very high concentrations when its yellow color can be seen. In order to increase the visibility of the gold cluster, the clusters can be used as catalysts for a developer containing silver ions. Silver precipitates around the cluster and this newly precipitated silver itself catalyzes further reduction of silver ions to metallic silver. By this process, with the gold cluster acting as a nucleation center, silver particles may be grown to almost any desired size by controlling the reaction time, temperature and other parameters. In this way, the formerly "invisible" gold cluster may now be visualized in commercial electron microscopes, in light microscopes, and with large silver grains, with the unaided eye.

Several specific examples are given that demonstrate the fundamental working principle:

A. Silver enhancement of gold cluster process. A number of silver developers are known in the literature and are available commercially that deposit silver around gold metal. These developers can be used to enhance the gold cluster conjugates; they grow very fine silver grains that appear more slowly than when applied to colloidal gold (metal). These grains are visible in the light microscope in usually 20–40 minutes and appear before any significant self nucleation of the silver. The developers of silver lactate, silver nitrate or silver acetate, with hydroquinone as a reducing agent in an acidic buffer such as sodium citrate, pH 3.5–4.0, are appropriate; in addition several commercial silver developers (e.g., Janssen Intense) were found to be satisfactory.

Improved silver enhancement was found to occur after a short exposure to short wave ultraviolet light, for 5–30 minutes for example. The silver grains then grew more rapidly and more final silver product was produced. Pretreatment of the clusters (before silver development) with a chemical reducing agent such as 0.1M sodium sulfite or 0.1M oxalic acid had a similar potentiating effect, although not as dramatic as the U.V. exposure. Gold cluster labeled antibodies showed the same behavior.

B. Discrimination of human colon carcinoma cells in the light microscope using gold cluster labeled antitumor antibodies and silver enhancement.

Human colon carcinoma cells (cell line LS180) were grown in tissue culture media. The cells were harvested with a brief trypsin treatment and centrifuged. They were then resuspended in phosphate buffered saline with 5% IgG free horse serum.

Assuming each call has approx. $10^6$ antibody binding sites, a ten fold molar excess over this of undecagold cluster-labeled 17-1A monoclonal antibody was applied. Cells were incubated at room temperature for one hour on a wrist shaker device. The cells were then centrifuged at 1100 rpm for 5 minutes and the supernatent discarded. Additional buffer was added to resuspend the cells and after 3 minutes they were centrifuged again. Three of these washes were done. As a control, melanoma cells (cell line WM 164) were also prepared in a similar fashion. Cells were concentrated onto glass microscope slides using a Cytospin device. Silver developer was added and after approximately 45 minutes the undecagold cluster labeled cells became brown in color, easily identifiable in the light microscope. UV exposure for 5 minutes prior to development enhanced this color. Control cells were clear and showed virtually no staining.

C. Visualization of immunoblots using undecagold labeled antibodies and silver enhancement. Apoferritin was dot blotted onto a nitrocellulose sheet and allowed to dry. A phosphate buffer (0.1M, pH$_7$) was then applied containing 5% bovine serum albumin to mask other protein binding sites. Gold cluster labeled rabbit antiferritin antibody was then incubated on the sheet for one hour followed by washing. After a 5 minute UV exposure a silver developer was applied which made the specifically bound antibody easily visible. Control sheets omitting the antigen on gold showed no colorization.

EXAMPLE 13

Preliminary in vitro testing of a monoclonal antibody to human colon carcinoma coupled to undecagold clusters shows that the Fab'-Au$_{11}$ conjugate retains its specificity for the tumor and does not bind to a control melanoma. The antibody used is "17-1A", commercially available from Centocor, Inc. These antibody-cluster conjugates were also assayed by electron microscopy, high pressure liquid chromatography, and spectroscopy and appeared to follow the normal course of results indicated in Examples 4 and 5. The number of gold clusters bound to each Fab' in this example was 0.7–1.0.

The in vitro test involved incubating the Fab'-Au$_{11}$ with either colorectal carcinoma cells or a control melanoma for one hour, centrifugation to isolate the cell-bound antibody, and assay of the bound antibody with a second antibody [to F(ab')$_2$] which was itself radiolabeled with iodine. A titer curve was produced. Compared to previous attempts at radiolabeling the 17-1A antibody by other methods, the present invention's results are qualitatively better since antibody activity and specificity were preserved.

Kinetic, or time course studies of the reaction of the 11-gold cluster with 17-1A Fab' fragments (incubations at 37° C.) show that after 30 minutes, 56% labeling occurs; after one hour, 79%; and after two hours, the reactions were complete. This is important since radioactive gold has a half life of 3.1 days, and therefore, short coupling reaction times are advantageous.

The amount of undecagold cluster necessary to label the 17-1A Fab' fragments was also studied. It was found that one gold cluster to one Fab' fragment resulted in more than 85% coupling. This high yield means that when high specific activity radiogold is used, there will be minimal amounts of waste generated, and approximately only enough radioactive gold need be produced for the dose being injected.

EXAMPLE 14

The 17-1A Fab' fragment-(radioactive gold)-undecagold cluster conjugate was incubated in vitro with tumor cells (LS180- a cell culture of human colon carcinoma) and non tumor cells (WM164 - a cell culture of melanoma as control) and the radioactivity of the gold was used to assay binding. As shown in Table 1 below, the radioactive gold was localized completely on the tumor cells with little (<0.4%, or background for F(ab')$_2$) on the non-tumor cells. This demonstrates the fact that gold cluster attachment to the anti-tumor antibody does not significantly diminish its specificity for tumor cells.

TABLE 1

In vitro cell binding of 17-1A-Au$_{11}$ conjugates. The data show the percent of applied radioactive gold bound to cells after incubation and washing. Each entry is an average (± s.d.) of 2 samples.

| Sample | % bound to tumor cells (human colon carcinoma) | % bound to control cells (melanoma) |
|---|---|---|
| Fab'-Au$_{11}$ | 7.80 ± 0.52 | 1.92 ± 0.17 |
| F(ab')$_2$-Au$_{11}$ | 16.13 + 0.02 | 0.30 ± 0.03 |
| IgG-Au$_{11}$ | 14.32 ± 0.92 | 0.77 ± 0.08 |
| Au$_{11}$ | 0.54 ± 0.04 | 0.51 ± 0.06 |

EXAMPLE 15

The folowing in vivo tests in mice assess both biodistribution with time and toxicity.

I. Toxicity and Biodistribution of Radioactive Gold Clusters (No Antibody)

Radioactive gold cluster was prepared as described that had a specific activity of 40 mCl/mg of gold metal. Various doses of gold cluster were injected into the tail vein of healthy mice: cluster containing 7.8 μg of gold metal into one group, 12.6 μg into another and 24 μg into the third. Each group consisted of 6 animals, for a total of 18 mice. Three mice from each group were sacrificed after 2 hours and the remaining 3 were terminated after 24 hours in order to determine the biodistribution in different organs as a function of time.

Results

One result was that no mice died or reacted unusually to the gold cluster during or following injection. The biodistribution studies showed that 44% of the clusters were excreted after 2 hours and 56% after 24 hours. Typically the blood had 2.8%, the spleen 0.4%, the stomach 0.4%, kidney 5.1%, bone 2.5%, gut and feces 3.3%, liver 19.3% and, carcass 13.7% of the injected amount after 24 hours. These numbers are % counts per organ normalized to 25 gm mice.

Conclusions

The highest dose of cluster injected, which contained 24 μg of gold metal, is approx. 6,000 times higher than what would be injected in a diagnostic or therapeutic dose. The fact that no noticeable side effects were observed indicates that the gold cluster by itself is probably not toxic. The biodistribution study indicated that more than half of the cluster (56%) was excreted by 24 hours. This is not unexpected because of its low molecular weight, about 5000 daltons.

II. Biodistribution of Gold Clusters Conjugated to Anti-Tumor Antibodies in Animals Bearing Human Tumors Nude mice bearing human colon carcinoma or melanoma tumors were injected with radioactive gold clusters conjugated to anti-tumor antibodies. Two antibodies were gold labeled, one (17-1A) against the human colon carcinoma and another non-relevant antibody, H$_{24}$B5 anti-influenza. The non-relevant tumor (melanoma) and non-relevant gold conjugated antibody (H$_{24}$B5) served as controls. A total of 53 mice were used. In order to assess the efficacy of using gold labeled Fab' versus whole IgG, both types of antibody were labeled and tested. In addition, two crosslinking arms between the gold cluster and antibody were used, one, as described in the preparation example, was N- methoxycarbonyl maleimide (NMCM), whereas the other was n-maleimidobenzoyl-N-hydroxysuccinimide ester (MBS), This was to test if a different covalent crosslinker between the gold cluster and antibody or antibody fragment yielded conjugates with different stabilities or body distributions in vivo.

Table 2 below sets forth the in vivo biodistribution data obtained from this study.

The labeled antibody against a human tumor concentrates on this tumor, whereas there is little accumulation in control tumors or with control antibodies. There does not appear to be a breakdown of the antibody and gold cluster which would be evidenced by a significant accumulation in the liver. This is a problem with many other radiolabeled antibody systems.

TABLE 2

In vivo biodistribution of radiogold cluster 17-1A conjugates. Data, taken 24 hr after injection is expressed in % of injected dose per gram of tissue. Tumor to normal tissue ratios are given in parentheses. Three or four mice for each sample were averaged; normalized to 25 g animals.

| Organ | Fab'-Au$_{11}$ | F(ab')$_2$-Au$_{11}$ | IgG-Au$_{11}$ |
| --- | --- | --- | --- |
| tumor | 6.4 ± 1.1 | 8.4 ± 0.6 | 8.0 ± 3.2 |
| blood | 3.4 ± 0.3(1.9) | 5.6 ± 0.4(1.5) | 3.2 ± 0.6(2.5) |
| spleen | 2.8 ± 0.4(2.3) | 6.4 ± 0.8(1.3) | 9.5 ± 0.3(0.8) |
| stomach | 0.57 ± 0.14(11.2) | 0.93 ± 0.19(9.1) | 0.69 ± 0.20(11.6) |
| kidneys | 103.0 ± 32(0.06) | 117.0 ± 20(0.1) | 17.1 ± 3.1(0.5) |
| heart | 1.7 ± 0.1(3.7) | 3.2 ± 0.4(3.4) | 2.6 ± 0.4(3.1) |
| lung | 2.5 ± 0.04(2.5) | 4.6 ± 0.1(1.8) | 3.4 ± 0.9(2.3) |
| muscle | 0.48 ± 0.06(13.2) | 0.98 ± 0.08(8.6) | 0.80 ± 0.23(10.0) |
| bone | 0.97 ± 0.02(6.6) | 2.4 ± 0.2(3.5) | 2.2 ± 0.3(3.6) |
| gut | 1.3 ± 0.1(5.) | 1.6 ± 0.2(5.3) | 1.1 ± 0.3(7.2) |
| liver | 5.6 ± 0.5(1.0) | 10.5 ± 0.4(0.8) | 4.6 ± 0.7(1.7) |
| Amount of MoAb injected per mouse (micrograms) | 0.8 | 0.7 | 19 |

EXAMPLE 16

Preparation of Au$_{55}$[PPh$_3$]$_{12}$Cl$_6$

The preparation of a large gold cluster was reported by G. Schmid, *Chem. Ber.*, 114, 3614 (1981), several years ago and was followed with some modification here. The large gold cluster produced by the Schmid process was unstable, unreactive and water insoluble. The modifications used in the instant process produce a cluster that is stable in solution, water soluble, and contains a reactive group for attachment to target molecules. A three neck flask fitted with a magnetic stir bar, condenser with a gas adapter, and glass tube gas inlet was charged with AuPPh$_3$Cl (0.281 g, 0.568 mmol) and dried benzene (11 ml) and warmed to 45° C. A large molar excess of diborane, generated by the slow dropwise addition of borontrifluoride etherate (6.4 ml, 52.0 mmol) to sodium borohydride (1.69 g, 44.7 mmol) in diglyme (15 ml), was passed through a dry-ice/isopropanol trap and then bubbled under nitrogen flow into the solution of AuPPh$_3$Cl in benzene. Over the course of diborane addition (about 35 minutes), the color of the solution became dark brown and dark solids were observed. The reaction was allowed to continue while the diborane generating flask was gently warmed to drive off most of the remaining diborane. The reaction mixture was filtered through a fine fitted glass filter and then washed with benzene and water. The residue was taken up in dichloromethane and measured for concentration through its UV-visible spectrum.

Au$_{55}$[PPh$_3$]$_{12}$Cl$_6$ can also be prepared using BH$_3$-tetrahydrofuran as the reducing agent. To a three necked 50 ml round bottom flask fitted with a gas inlet, addition funnel with rubber septum, and condenser with gas outlet was added a magnetic stir bar and AuP(C$_6$H$_5$)$_3$Cl(0.157 g, 0.317 mmol). After flushing the flask with N$_2$, 5 ml of freshly distilled toluene was added and the mixture stirred at 50° C. A solution of 2 ml 1M BH$_3$-tetrahydrofuran in 6 ml toluene was placed into the addition funnel and then added dropwise over 30 min to the AuP(C$_6$H$_5$)$_3$Cl. After the addition was completed, the reaction mixture was stirred for an additional 30 min, cooled to room temperature (r.t.), and then filtered in air through a fine glass fit. The residue was then treated similarly to the residue obtained after diborane reduction according to the previous description.

EXAMPLE 17

Preparation of Derivatized Au$_{55}$ Clusters

From the crude product obtained in Example 16, other clusters were obtained by exchange reactions or by exchange and subsequent degradation reactions. The exchange reactions resulted in the replacement of a number of the triphenylphosphines by biocompatible phosphines, such as a mixture of P(C$_6$H$_4$CONHCH$_3$)$_3$P(C$_6$H$_4$CONHCH$_3$)$_2$(C$_6$H$_4$CONH(CH$_2$)$_3$NH$_2$), and tris-4-carboxyphenylphosphine. The derivatized large cluster obtained in quite stable, but it can be degraded intentionally (by acid treatment, for example) to smaller clusters of interest, identified by scanning transmission electron microscopy (STEM) and UV-visible spectroscopy as a cluster with 13 gold atoms.

As an example of the exchange reaction, the preparation of a derivatize for coupling to proteins is described. A methanol solution containing 24 equivalents of the average mass of the derivatized phosphine mixture was added to the crude product and stirred overnight. The product from the phosphine exchange reaction was extracted into a 0.02M ammonium acetate buffer pH 5.8. The aqueous solution was concentrated, applied to a 500 ml Amicon GH-25 column, a gel filtration medium, and eluted with 0.6 molar triethylammonium hydrogen carbonate/5% (v/v) methanol.

EXAMPLE 18

Activation of Derivatized Au$_{55}$ Clusters for Protein Labeling

The chromatography procedure described in Example 17 yielded fractions containing the cluster and little or no excess phosphine or other impurities. These fractions were pooled and then reacted with a heterofunctional coupling reagent to yield an activated cluster. When one functional group on the coupling reagent reacts with a group on the phosphine ligand and another, different functional group on the coupling agent reacts with a group on a protein, the cluster and protein are chemically bound. Many coupling reagents are readily available. We have used two of these, N-methoxycarbonyl maleimide (NMCM) or m-Maleimidobenzoyl-N-hydroxysuccinimide ester (m-MBS), for coupling gold clusters with free amines to proteins.

The following is an example of the coupling procedure using m-MBS. Derivatized $Au_{55}$ cluster prepared from exchange with a 10:1 ratio of $P(C_6H_4CONHCH_3)_3$ to $P(C_6H_4CONHCH_3)_2(C_6H_4CONH(CH_2)_3NH_2)$ (56.8 nanomoles) dissolved in methanol/0.2M sodium phosphate pH 7 (~1 ml) was reacted with 0.4 mg m-MBS (1270 nanomoles) in dimethyl sulfoxide (50 microliters) for 40 min. The reaction mixture was chromatographed on Amicon GH-25 using 0.2M sodium phosphate pH 7 as the eluent and the fractions containing the activated cluster were pooled.

EXAMPLE 19

Coupling of Activated Clusters to Proteins

Once activated and purified, the derivatized $Au_{55}$ cluster can be reacted with a protein. Specifically, the clusters activated with NMCM or m-MBS should react with reagents bearing an available sulfhydryl group (—SH), such as Fab' antibody fragments. This has been achieved with several rabbit polyclonal antibodies and a mouse monoclonal antihuman brain tumor antibody (EGF 425). The resultant antibody-$Au_{55}$ cluster complexes were examined by electron microscopy to determine the extent of complexation of the cluster to the protein, which showed that up to 80% of the antibodies had an $Au_{55}$ attached.

EXAMPLE 20

Labeling Antitumor Monoclonal Antibody with $Au_{55}$

The following describes the attachment of the $Au_{55}$ cluster to a monoclonal antibody which binds to a human neuroblastoma (brain tumor).

1.0 mg of EGF-425 monoclonal antibody to human brain tumor was digested with 2% pepsin by weight at pH 4.5 (in 0.1M citrate buffer) at 37° C. concentrating the solution using a Centricon C-30 device (Amicon) and applying the concentrate to a Zorbax GF-250 column (DuPont) in 0.2M sodium phosphate buffer pH 7.0. 0.3 mg of the F(ab')$_2$ antibody fragments produced was reduced by reacting with 20 mM dithiothreitol (DTT) for 2 hr at r.t. The DTT was then removed by running the sample through a gel filtration column (Zorbax GF-250). The purified Fab' antibody fragments were then mixed with a 3-fold molar excess of the "activated" (containing maleimide) $Au_{55}$ cluster and were allowed to react overnight at 4° C.

The reaction mixture was then purified by high-pressure liquid chromatography (HPLC) using a Zorbax GF-250 column. This separated the unbound (excess $Au_{55}$ cluster from the antibody with $Au_{55}$ cluster attached.

EXAMPLE 21

In Vitro Testing of Antitumor Monoclonal Antibody Attached to $Au_{55}$

EGF-425, a monoclonal antibody to human brain tumor, was labeled with $Au_{55}$ as described in Example 20. Serial dilutions (5 g to 1.2 ng) of this labeled antibody were incubated with either 250,000 cells from cultured human brain tumor or with a control melanoma cell line. After an incubation time of 1 hr at r.t. with shaking, the cells were washed three times with buffer. A second antibody, $^{125}$I-labeled rabbit antimouse (F(ab')$_2$ specific), was then incubated with the cells for 1 hr and rinsed three times as before. Results from this radioimmunoassay indicate little loss of immunoreactivity and immunospecificity as a result of coupling the $Au_{55}$ onto the antibody.

EXAMPLE 22

Preparation of $Au_{55}$ Labeled Fab' and F(ab')$_2$ Fragments

Both Fab' and F(ab')$_2$ antibody fragments have been labeled with the 55-gold atom cluster using both monoclonal and polyclonal antibodies. The monoclonal antibody used was EGF-425, an antibody specific for human brain tumors. The polyclonal antibodies used were produced in rabbits and were specific for horse spleen ferritin and human red blood cells.

The formation of Fab'-$Au_{55}$ conjugates is described in Example 20 above. F(ab')$_2$-$Au_{55}$ is prepared as follows: The $Au_{55}$ cluster has 12 triphenylphosphine derivatives on its surface. It is made in monofunctional form (so that it will react with only one Fab' antibody fragment, to form Fab'-$Au_{55}$) by mixing a proportion of unreactive derivatized phosphines [P(PhCONHCH$_3$)$_3$; Ph-phenyl] and those containing an amine [(H$_3$CHNOCPh)$_2$ P(PhCONH(CH$_2$)$_3$NH$_2$]. These are mixed in the phosphine exchange reaction step of $Au_{55}$ preparation (step b) described above. The ratio of these two phosphines is adjusted to ~11:1 in order to maximize to yield of monoamine cluster. As described above, the amine is converted into a maleimide which will covalently attach to an Fab' antibody fragment at its free sulfhydryl in the hinge region. To produce F(ab')$_2$-$Au_{55}$, the ratio of the amine containing phosphine is increased to ~5:1 to yield mostly clusters containing ten unreactive phosphines and two with amines. These diamino $Au_{55}$ clusters then become dimaleimide $Au_{55}$ clusters and can covalently attach two Fab' fragments producing F(ab')$_2$-$Au_{55}$.

Both Fab'-$Au_{55}$ and F(ab')$_2$-$Au_{55}$ products produced as described above were separated on a gel exclusion HPLC column (DuPont Zorbax GF-250). These products were then verified by UV-visible spectroscopy and electron microscopy.

Mercaptoethylamine (MEA) is a commercially available reducing reagent that can be used to produce free —SH groups in the hinge region on otherwise intact whole antibody molecules. MEA was used for this purpose and additionally, for the mild reduction of F(ab')$_2$ to Fab' fragments. The antibodies used were specific to horse spleen ferritin and to human red blood cells.

In these procedures the protein was reacted with 10.0 mM MEA in 0.1M sodium phosphate, pH 6.0/5 mM EDTA at r.t. for 1 hr and then purified over Amicon GH-25 using 0.02M sodium phosphate, pH 6.5/1 mM EDTA/150 mM NaCl as the eluant. These purified fractions were reacted with a three to ten fold excess of activated gold clusters that was isolated in the same buffer at 4° C. overnight. The products from the coupling reactions were purified on a gel exclusion HPLC column (Pharmacia Superose-6) using 5 mM sodium phosphate, pH 8/150 mM NaCl as the eluant. These conjugates retain the specific activity of the original antibody. The $Au_{55}$ cluster anti-horse spleen ferritin conjugate binds to ferritin and the $Au_{55}$ cluster anti-human red blood cell conjugates binds to red blood cells.

EXAMPLE 23

$Au_{13}$ Cluster—Preparation 27 mol of the derivatized triphenyl phosphine, $P(PhCONH(CH_2)_3NH_2)_3$, was dissolved in 1 ml methanol and mixed with 6 mg AuCN in 2 ml of ethanol. After a reaction time of 40 min at r.t., 27 μmol of an ethanolic 0.05M solution of $NaBH_4$ was added over a 2 hr period. Subsequently, 0.15 ml of acetone was added. The solvent was evaporated and the product redissolved in 0.1M citrate buffer, pH 5. It was purified by filtration through a 0.2 μfilter then run on an Amicon GH-25 gel filtration column, 0.66×50 cm, in the above buffer. The purified product was analyzed using UV-visible spectroscopy and electron microscopy. The product was $Au_{13}[P(PhCONH(CH_2)_3NH_2]_{10}$.

EXAMPLE 24

$Au_{13}$ Cluster Conjugates

The polyamino $Au_{13}$ cluster synthesized as described in Example 23 was studied to determine its reactivity and usefulness for covalent attachment to proteins and other molecules. As a test substrate, Affigel 10 (BioRad) was used. This is a slurry of acrylamide beads that contain N-hydroxysuccinimide esters on them which should specifically react with amines to form a covalent product. One nmole of $Au_{13}$ cluster was reacted with 0.5 ml of Affigel 10 for 1 hr and r.t. with shaking. Afterwards, the mixture was filtered through a 0.2 μm filter and rinsed. No $Au_{13}$ cluster came through with the filtrate indicating it had all attached covalently to the beads.

EXAMPLE 25

Crosslinking of Gold Clusters

The derivatized gold clusters containing 11, 13 and 55 gold atoms prepared as described above have reasonable stability at r.t. in aqueous solvents. The underivatized $Au_{55}$ $(PPh_3)_{12}$ is only stable for approximately a day or two in solution. The derivatized $Au_{55}$ cluster is stable and remains virtually intact over a period of months. The solution stability of the different clusters ($Au_{55}$, $Au_{13}$, $Au_{11}$, $Au_9$, $Au_6$, etc.) varies. Also, the stability with regard to various treatments and conditions varies. For example, the $Au_{55}$ cluster deteriorates rapidly above 70° C., but the $Au_{11}$ cluster is perfectly stable at 100° C.

Chemical stability is another factor. It was found that a derivatized $Au_{13}$ cluster was stable in 1N HCl, 1N $HNO_3$, and 1N NaOH but degraded upon addition of 1M glutathione, 1M KCN, or 30% $H_2O_2$. For some applications of these clusters, such as in vivo use or to extend shelf life of cluster reagents, it may be desirable to crosslink the organic shell of the cluster to improve its stability. By using approprite derivatized phosphines and chemical or photoactivated crosslinking reagents, this has now been shown to be feasible. A few specific examples are provided, but the methodology is applicable to all nuclearity clusters ($Au_{55}$, $Au_{13}$, $Au_{11}$, $Au_9$ and $Au_6$).

a. Chemical Crosslinking of $Au_{13}$ Cluster

The cluster $Au_{13}$ $[P(PhCONH(CH_2)_3NH_2)_3]_{10}$ was prepared as described in Example 23. Two nmol of $Au_{13}$ cluster at pH 5.0 was incubated with glutaraldehyde or glyoxal in a range of molar ratios from 0.2 to 1000 of dialdehyde to amine. After an incubation period at r.t. (a range of 30 min to 16 hr was used), a 10-fold molar excess of glycine was added to quench the remaining aldehyde. After 15 min, the Schiff bases formed were reduced by adding a 10-fold molar excess of an ethanolic solution of sodium cyanoborohydride. After 30 min, a few drops of acetone were added to inactivate the borohydride. Chemical stability of the cluster was dramatically increased using 100-fold molar excess of glutaraldehyde for 1 hr, The glyoxal and other concentrations and reaction times were less effective.

b. Photocrosslinking of $Au_{13}$ Cluster

Another method of strengthening the organic outer shell of these clusters is by the use of photocrosslinking reagents. These can first be chemically attached to, say, amines on the cluster. Then UV light can be used to activate the other end of the crosslinker to form covalent bonds with any nearby organic chain. Two different length photocrosslinking reagents were tried.

Two nmol of the $Au_{13}$ $[P(PhCONH(CH_2)_3NH_2)_3]_{10}$ cluster in 0.1M sodium citrate buffer, pH 5, was incubated with the crosslinking reagent, N-hydroxysuccinimidyl-4-azidosalicylic acid (NHS-ASA). A range of amounts was tried, from 1 to 100-fold molar excess over the number of amines in the cluster. Incubation was carried out in the dark for 30 min. The solution was exposed to UV light (Ultraviolet Products Inc., Lamp R-52) at 4 cm for 5 min. The product was purified on a 0.66×50 cm column of GH-25 (Amicon) using the buffer 0.36M triethylammonium bicarbonate/70% methanol in water. Alternately, these last two steps were reversed so that unreacted crosslinker was removed on the column before UV treatment.

The crosslinked cluster stability was quantitated by observing the decrease in optical density at 346 and 420 nm in a spectrophotometer at regular intervals after adding KCN or glutathione. One hundred μl of cluster (1 μMolar) was mixed with 20 μl of 0.1M KCN. For the cluster reacted with 100-fold molar excess of NHS-ASA, 33% of the cluster remained after this treatment after 30 min, with no further degradation. Noncrosslinked cluster was completely destroyed after 2 min under these conditions.

A longer photocrosslinking reagent was also used, sulfosuccinimidyl 6-(4'-azido-2'-nitrophenylamino) hexanoate (sulfo-SANPAH). The procedure was identical to that described above. For 100-fold initial excess of crosslinker, the resulting cluster product was 100% stable to KCN indefinitely, whereas uncrosslinked cluster was completely destroyed in 2 min.

It is, therefore, possible to greatly improve the chemical stability of derivatized gold clusters by crosslinking.

EXAMPLE 26

Multidentate Ligands

The introduction of multidentate ligands, in place of the triarylphosphines, can decrease the rate of any limited decomposition of the gold cluster. Generally multidentate ligands impart stability to coordination compounds that decompose by loss of the ligands (unimolecularly or otherwise).

A method to form a connected ligand sphere has been described in Example 25—crosslinking coordinated ligands. Another approach is the exchange of bis-, or tris-phosphines for the tri-arylphosphines of the initially formed large gold cluster. In a preliminary experiment, 1,6-bis(diphenylphosphine)hexane was exchanged for the triphenylphosphine of the starting compound. STEM microscopy of the product indicated that the cluster was substantially more stable in the electron beam.

EXAMPLE 27

Electron Microscopy of Derivitized $Au_{55}$ Clusters

Several derivatized $Au_{55}$ clusters were applied to thin carbon films that were supported by a holey carbon film and a titanium grid. The clusters examined by electron microscopy were $Au_{55}$ clusters with free amines or carboxyl groups, and the protein bound complexes, Fab'-$Au_{55}$ and F(ab')$_2$.

The STEM examination demonstrated the stability of the large clusters to an electron beam. Large accumulated doses of beam energy result in small fractional mass loss indicating limited decomposition. Translational movement of the clusters under the beam proved to be negligible, thus providing evidence that these clusters can be used for positional labeling.

EXAMPLE 28

Silver Enhancement of $Au_{55}$ Gold Clusters

A standard silver developer containing silver ions and hydroquinone as a reducing agent was applied to derivatized $Au_{55}$ gold cluster and to antibody bound $Au_{55}$ gold cluster. This produced enhanced particle growth that was monitored by optical microscopy.

An example of silver enhanced detection of antibody binding, 5 μl spots containing successive dilutions of apoferritin were spotted onto a nitro-cellulose membrane. After the rest of the membrane was blocked to inhibit nonspecific antibody absorption, the membrane was washed with a alution of the $Au_{55}$ cluster anti-ferritin conjugate. Reaction with a silver developer showed the gold cluster's presence indicating that this is a sensitive method for the immunological detection of proteins.

EXAMPLE 29

Immunoblot Blots Secondary Antibody Technique

Example 28 discusses the use of gold cluster-antibody conjugates and silver enhanced detection of antigens utilizing the conjugates as primary antibodies. Primary antibodies bind to the anttgen and detection, via reaction of a silver reagent with the gold cluster follows directly.

Gold conjugates can be made more generally useful by preparation of conjugates that function as secondary antibodies. In this case the antibodies are not specific to the antigen, but are active against the primary antibody that is itself specific to the antigen. This permits use of the cluster-secondary antibody conjugate in detection of a large variety of antigens. This property reduces the need to prepare a large number of antigen specific gold cluster conjugates. Most primary antibodies are developed in mice, goats, or rabbits. By using only 3 gold cluster antibody conjugates (gold-anti-mouse, -goat, -rabbit), thousands of antigens may be detected. The primary antibody (from mouse, goat, or rabbit) is first bound to the antigen. Then the appropriate gold cluster antibody conjugate is applied for detection (gold anti-mouse, -goat, or -rabbit). Another important benefit occurs in those instances where more than one secondary antibody conjugate binds to the primary antibody. This case provides a mechanism for amplification of the silver enhancement reaction. Where there are more clusters there is a greater number of silver aggregates formed and sensitivity can be increased.

We claim:

1. An antibody-gold cluster conjugate wherein the antibody is covalently bound to the cluster and the gold cluster is the monomaleimide undecagold cluster shown in FIG. 3.

2. An antibody fragment-gold cluster conjugate wherein the antibody fragment is covalently bound to the cluster and the gold cluster is the monomaleimide undecagold cluster shown in FIG. 3.

3. An antibody-gold cluster conjugate of claim 1 wherein the antibody is covalently bound to at least one radioactive undecagold cluster.

4. An antibody fragment-gold cluster conjugate of claim 2 wherein the antibody fragment is covalently bound to at least one radioactive undecagold cluster.

5. An antibody-gold cluster conjugate wherein the antibody is covalently bound to the cluster and the gold cluster has the formula $Au_{13}[P(Ph\text{-}CONH(CH_2)_3)NH_2]_{10}$.

6. An antibody fragment-gold cluster conjugate wherein the antibody fragment is covalently bound to the cluster and the gold cluster has the formula $Au_{13}[P(PhCONH(CH_2)_3)NH_2]_{10}$.

* * * * *